(12) United States Patent
Masuda et al.

(10) Patent No.: US 7,090,980 B2
(45) Date of Patent: Aug. 15, 2006

(54) METHOD OF DETECTING ACID-FAST BACTERIA USING RIBOSOMAL RNA AS TARGET

(75) Inventors: Noriyoshi Masuda, Tokyo (JP); Yuichi Isawa, Kanagawa-ken (JP); Ryuichi Horie, Kanagawa-ken (JP); Kiyoshi Yasukawa, Kanagawa-ken (JP)

(73) Assignee: Tosoh Corporation, Yamaguchi-ken (JP)

( * ) Notice: Subject to any disclaimer, the term of this patent is extended or adjusted under 35 U.S.C. 154(b) by 0 days.

(21) Appl. No.: 10/737,894

(22) Filed: Dec. 18, 2003

(65) Prior Publication Data

US 2004/0161783 A1 Aug. 19, 2004

(30) Foreign Application Priority Data

Dec. 19, 2002 (JP) ............................. 2002-368230

(51) Int. Cl.
*C12Q 1/68* (2006.01)
*C07H 21/02* (2006.01)
*C07H 21/04* (2006.01)
*A61K 39/04* (2006.01)

(52) U.S. Cl. .................... 435/6; 424/184.1; 424/234.1; 424/248.1; 435/253.1; 435/501; 536/23.1; 536/23.7; 536/24.3; 536/24.32

(58) Field of Classification Search ............ 424/184.1, 424/234.1, 248.1; 435/6, 253.1; 436/501; 536/23.1, 23.7, 24.3, 24.32
See application file for complete search history.

(56) References Cited

U.S. PATENT DOCUMENTS 5,422,242 A * 6/1995 Young .......................... 435/6

| | | |
|---|---|---|
| 5,712,095 A | 1/1998 | Britschgi et al. |
| 5,770,373 A | 6/1998 | Britschgi et al. |
| 5,908,744 A | 6/1999 | McAllister et al. |
| 5,925,518 A | 7/1999 | Earle et al. |

FOREIGN PATENT DOCUMENTS

| | | |
|---|---|---|
| EP | 0 528 306 A3 | 2/1993 |
| EP | 0 529 985 A1 | 3/1993 |
| EP | 0 969 101 A1 | 1/2000 |
| EP | 1 076 099 A2 | 2/2001 |
| WO | WO 01/44510 A2 | 6/2001 |
| WO | WO 01/66797 A2 | 9/2001 |

OTHER PUBLICATIONS

Andrew Chin, "On the Preparation and Utilization of Isolated and Purified Oligonucleotides"; The University of North Carolina School of Law; Mar. 9, 2002.

Hughes M S et al: "Identification by 16S rRNA Gene Analyses of a Potential Novel Mycobacterial Species as an Etiological Agent of Canine Leproid Granuloma Syndrome" Journal of Clinical Microbiology, Washington, DC. US, vol. 38, No. 3, Mar. 2000; pp. 953-959, XP002190512.

Database EMBL 'Online!; M. Tuberculosis 16srRNA gene PCR primer #2, May 23, 2001; Toyobo KK.; "M Tuberculosis 16srRNA gene PCR primer #2" retrieve from EBI Database accession No. AAF77540, XP002279274.

* cited by examiner

*Primary Examiner*—Rodney P Swartz
(74) *Attorney, Agent, or Firm*—Sughrue Mion, PLLC (57) ABSTRACT

A method of detecting a specific acid-fast bacterium, wherein primers having nucleotide sequences homologous or complementary to the specific regions in the rRNAs of the specific acid-fast bacterium are used to specifically amplify only the rRNAs of the specific acid-fast bacterium.

13 Claims, 3 Drawing Sheets

Fig. 1(A): Combination (a)

Fig. 1(B): Combination (b)

Fig. 3(A): Combination (a)
Unit: cells/1 mL sputum

Fig. 3(B): Combination (b)
Unit: cells/1 mL sputum

SEQUENCE LISTING

<160> NUMBER OF SEQ ID NOS: 18

<210> SEQ ID NO 1
<211> LENGTH: 23
<212> TYPE: DNA
<213> ORGANISM: Artificial Sequence
<220> FEATURE:
<223> OTHER INFORMATION: Primer MYR-1F-10-T7

<400> SEQUENCE: 1
cggaaaggtc tcttcggaga tac                 23

<210> SEQ ID NO 2
<211> LENGTH: 18
<212> TYPE: DNA
<213> ORGANISM: Artificial Sequence
<220> FEATURE:
<223> OTHER INFORMATION: Primer MYR-3RT18

<400> SEQUENCE: 2
acaagacatg catcccgt                       18

<210> SEQ ID NO 3
<211> LENGTH: 23
<212> TYPE: DNA
<213> ORGANISM: Artificial Sequence
<220> FEATURE:
<223> OTHER INFORMATION: Primer MYR-1FA-10-T7

<400> SEQUENCE: 3
cggaaaggcc tcttcggagg tac                 23

<210> SEQ ID NO 4
<211> LENGTH: 18
<212> TYPE: DNA
<213> ORGANISM: Artificial Sequence
<220> FEATURE:
<223> OTHER INFORMATION: Primer MYR-3RA18

<400> SEQUENCE: 4
agaagacatg cgtcttga                       18

```
<210> SEQ ID NO 5
<211> LENGTH: 23
<212> TYPE: DNA
<213> ORGANISM: Artificial Sequence
<220> FEATURE:
<223> OTHER INFORMATION: Primer MYR-1FI-10-T7

<400> SEQUENCE: 5
cggaaaggcc ccttcggggg tac                                          23

<210> SEQ ID NO 6
<211> LENGTH: 18
<212> TYPE: DNA
<213> ORGANISM: Artificial Sequence
<220> FEATURE:
<223> OTHER INFORMATION: Primer MYR-3RI18

<400> SEQUENCE: 6
taaagacatg cgcctaaa                                                18

<210> SEQ ID NO 7
<211> LENGTH: 23
<212> TYPE: DNA
<213> ORGANISM: Artificial Sequence
<220> FEATURE:
<223> OTHER INFORMATION: Primer MYR-1FK-10-T7

<400> SEQUENCE: 7
cggaaaggtc tcttcggaga cac                                          23

<210> SEQ ID NO 8
<211> LENGTH: 18
<212> TYPE: DNA
<213> ORGANISM: Artificial Sequence
<220> FEATURE:
<223> OTHER INFORMATION: Primer MYR-3RK18

<400> SEQUENCE: 8
acaaggcatg cgccaagt                                                18

<210> SEQ ID NO 9
<211> LENGTH: 20
<212> TYPE: DNA
<213> ORGANISM: Artificial Sequence
<220> FEATURE:
<223> OTHER INFORMATION: Probe YO-MYR-S-G

<400> SEQUENCE: 9
agacccagtt tcccaggctt                                              20

<210> SEQ ID NO 10
<211> LENGTH: 24
<212> TYPE: DNA
<213> ORGANISM: Artificial Sequence
<220> FEATURE:
<223> OTHER INFORMATION: Cleavage primer MYR-1S-10

<400> SEQUENCE: 10
tttccgttcg acttgcatgt gtta                                         24

<210> SEQ ID NO 11
<211> LENGTH: 24
<212> TYPE: DNA
<213> ORGANISM: Artificial Sequence
<220> FEATURE:
<223> OTHER INFORMATION: Primer MTR-1S
```

<400> SEQUENCE: 11
tttcccaggc ttatcccgaa gtgc                                          24

<210> SEQ ID NO 12
<211> LENGTH: 51
<212> TYPE: DNA
<213> ORGANISM: Artificial Sequence
<220> FEATURE:
<223> OTHER INFORMATION: Primer MTR-1F

<400> SEQUENCE: 12
aattctaata cgactcacta gggagagg gaaactgggt ctaataccgg a               51

<210> SEQ ID NO 13
<211> LENGTH: 51
<212> TYPE: DNA
<213> ORGANISM: Artificial Sequence
<220> FEATURE:
<223> OTHER INFORMATION: Primer MYR-1F-10

<400> SEQUENCE: 13
aattctaata cgactcacta gggagacg gaaaggtctc ttcggagata c               51

<210> SEQ ID NO 14
<211> LENGTH: 20
<212> TYPE: DNA
<213> ORGANISM: Artificial Sequence
<220> FEATURE:
<223> OTHER INFORMATION: Primer MTR-7R

<400> SEQUENCE: 14
agaacccgga ccttcgtcga                                               20

<210> SEQ ID NO 15
<211> LENGTH: 20
<212> TYPE: DNA
<213> ORGANISM: Artificial Sequence
<220> FEATURE:
<223> OTHER INFORMATION: Probe YO-MT 16S-S-G

<400> SEQUENCE: 15
ccacaagaca tgcatcccgt                                               20

<210> SEQ ID NO 16
<211> LENGTH: 51
<212> TYPE: DNA
<213> ORGANISM: Artificial Sequence
<220> FEATURE:
<223> OTHER INFORMATION: Primer MYR-1FA-10

<400> SEQUENCE: 16
aattctaata cgactcacta gggagacg gaaaggcctc ttcggaggta c               51

<210> SEQ ID NO 17
<211> LENGTH: 51
<212> TYPE: DNA
<213> ORGANISM: Artificial Sequence
<220> FEATURE:
<223> OTHER INFORMATION: Primer MYR-1FI-10

<400> SEQUENCE: 17
aattctaata cgactcacta gggagacg gaaaggcccc ttcggggta c                51

<210> SEQ ID NO 18

<211> LENGTH: 51
<212> TYPE: DNA
<213> ORGANISM: Artificial Sequence
<220> FEATURE:
<223> OTHER INFORMATION: Primer MYR-1FK-10

<400> SEQUENCE: 18
aattctaata cgactcacta tagggagacg gaaaggtctc ttcggagaca c       51

METHOD OF DETECTING ACID-FAST BACTERIA USING RIBOSOMAL RNA AS TARGET

The present invention relates to a method for detection of the ribosomal RNA (rRNA) from a specific acid-fast bacterium.

The rRNAs are the RNAs constituting the ribosome particles and present both in bacteria and in higher organisms. Bacteria have three rRNAs (the 23S rRNA, the 16S rRNA and the 5S RNA). Among them, the 16S rRNA is used as a taxonomic mark for classification of bacteria. The sequences of the 16S rRNAs from many bacteria have been determined and stored in databases. Many test kits using the 16S rRNA as the mark have been developed on the basis of these sequence data.

For genetic tests detecting certain acid-fast bacteria such as *Mycobacterium tuberculosis*, *Mycobacterium avium* and *Mycobacterium intracellulare*, the use of distinctive regions of the 16S rRNA gene or the 16S rRNA sequence from the target acid-fast bacterium which distinguish the target acid-fast bacterium from other acid-fast bacteria as DNA probes has been reported (for example, patent document 1 and patent document 2) and is seen in commercially available test kits. These kits are designed so that the primers used for gene amplification bind to regions common to acid-fast bacteria.

Patent document 1 —Japanese Patent Publication No. 3116353

Patent document 2 —Japanese Patent Publication No. 2675723

It is known that detection of specific acid-fast bacteria such as *Mycobacterium tuberculosis*, *Mycobacterium avium*, *Mycobacterium intracellulare* or *Mycobacterium kansasii* by genetic tests is less sensitive than that by selective cultivation and needs higher sensitivity. However, because distinctive regions in the 16S rRNA of a specific acid-fast bacterium are limited, the limited choice of probe sequences is an obstacle to high sensitivity.

Therefore, the object of the present invention is to provide a sensitive genetic test for detection of a specific acid-fast bacterium.

The present inventors conducted extensive research to construct a detection method-based on the 16S rRNA and revealed that the use of primers which bind to regions common to acid-fast bacteria accounts for the low sensitivity because they also allow nontarget acid-fast bacteria to amplify competitively. In addition, the present inventors demonstrated that the use of primers specific for a target acid-fast bacterium allows only the target acid-fast bacterium to amplify and therefore makes it possible to specifically detect the target bacteria with a probe which binds to a region common to acid-fast bacteria.

The invention defined in Claim 1 of the present application provides a method of detecting a specific acid-fast bacterium, wherein primers having nucleotide sequences homologous or complementary to the specific regions in the rRNAs of the specific acid-fast bacterium are used to specifically amplify only the rRNAs of the specific acid-fast bacterium.

The invention defined in Claim 2 of the present application provides an oligonucleotide for DNA elongation which binds to a specific region of the 16S rRNA of *Mycobacterium tuberculosis* and consists of at least 10 nucleotides in either SEQ ID NO:1 or SEQ ID NO:2.

The invention defined in Claim 3 of the present application provides an oligonucleotide for DNA elongation which binds to a specific region of the 16S rRNA of a nontuberculous acid-fast bacterium, *Mycobacterium avium*, and consists of at least 10 nucleotides in either SEQ ID NO:3 or SEQ ID NO:4.

The invention defined in Claim 4 of the present application provides an oligonucleotide for DNA elongation which binds to a specific region of the 16S rRNA of a nontuberculous acid-fast bacterium, *Mycobacterium intracellulare*, and consists of at least 10 nucleotides in either SEQ ID NO:5 or SEQ ID NO:6.

The invention defined in Claim 5 of the present application provides an oligonucleotide for DNA elongation which binds to a specific region of the 16S rRNA of a nontuberculous bacterium, *Mycobacterium kansasii*, and consists of at least 10 nucleotides in either SEQ ID NO:7 or SEQ ID NO:8.

The invention defined in Claim 6 of the present application provides a detection method using an RNA amplification step for amplifying the 16S rRNA from a specific acid-fast bacterium which comprises synthesizing a cDNA by the action of an RNA-dependent DNA polymerase by using a specific sequence in the 16S rRNA from the specific acid-fast bacterium present in a sample as a template, degrading the RNA strand in the resulting RNA-DNA double strand by an enzyme having a ribonuclease H activity to give a single-stranded DNA, forming a double-stranded DNA having a promoter sequence which can be transcribed into an RNA homologous or complementary to the specific sequence by using the single-stranded DNA as a template by the action of a DNA-dependent DNA polymerase, and then transcribing the double-stranded DNA into an RNA transcript, which acts as a template in the subsequent cDNA synthesis by the RNA-dependent DNA polymerase, wherein a first primer containing a sequence homologous to part of the 16S rRNA from the specific acid-fast bacterium to be amplified and a second primer containing a sequence complementary to part of the 16S rRNA from the specific acid-fast bacterium to be amplified (either of which additionally has a promoter sequence for the RNA polymerase at the 5' end) are used.

The invention defined in Claim 7 of the present application provides the method according to Claim 6, wherein the specific acid-fast bacteria is *Mycobacterium tuberculosis*, the first primer consists of at least 10 consecutive nucleotides in SEQ ID NO:1 or in the sequence complementary to SEQ ID NO:1, and the second primer consists of at least 10 consecutive nucleotides in SEQ ID NO:2 or in the sequence complementary to SEQ ID NO:2.

The invention defined in Claim 8 of the present application provides the method according to Claim 6, wherein the specific acid-fast bacterium is *Mycobacterium avium*, the first primer consists of at least 10 consecutive nucleotides in SEQ ID NO:3 or in the sequence complementary to SEQ ID NO:3, and the second primer consists of at least 10 consecutive nucleotides in SEQ ID NO:4 or in the sequence complementary to SEQ ID NO:4.

The invention defined in Claim 9 of the present application provides the method according to Claim 6, wherein the specific acid-fast bacterium is *Mycobacterium intracellulare*, the first primer consists of at least 10 consecutive nucleotides in SEQ ID NO:5 or in the sequence complementary to SEQ ID NO:5, and the second primer consists of at least 10 consecutive nucleotides in SEQ ID NO:6 or in the sequence complementary to SEQ ID NO:6.

The invention defined in Claim 10 of the present application provides the method according to Claim 6, wherein the specific acid-fast bacterium is *Mycobacterium kansasii*, the first primer consists of at least 10 consecutive nucleotides in SEQ ID NO:7 or in the sequence complementary to SEQ ID NO:7, and the second primer consists of at least 10 consecutive nucleotides in SEQ ID NO:8 or in the sequence complementary to SEQ ID NO:8.

The invention defined in Claim 11 of the present application provides the method according to any of Claims 6 to 10, which comprises conducting the RNA amplification step in the presence of an oligonucleotide probe (having a sequence different from those of the first primer and the second primer) which can specifically bind to the RNA transcript resulting from the amplification and is labeled with an fluorescent intercalative dye, and measuring the change in the fluorescence from the reaction solution.

The invention defined in Claim 12 of the present application provides the method according to Claim 11, wherein the oligonucleotide labeled with a fluorescent intercalative dye is designed to hybridize with at least part of the RNA transcript and alters its fluorescence upon hybridization. The invention defined in Claim 13 of the present application provides the method according to Claim 12, wherein the oligonucleotide labeled with a fluorescent intercalative dye has a sequence consisting of or complementary to at least 10 consecutive nucleotides in SEQ ID NO:9.

FIG. 1 shows the locations of the respective oligonucleotides used in Examples 1 and 2 and the amplified regions [(A): the combination (a), (B): the combination (b)]. The bases in the 16S rRNA base sequence (GenBank No. Z83862) are numbered from the starting position of the 16S rRNA, and the double-headed arrows indicate the regions distinctive of *Mycobacterium tuberculosis* among the 16S rRNAs from acid-fast bacteria.

FIG. 2 is a (negative) photograph showing the results of electrophoresis of RNA amplification from the nucleic acid extract sample from acid-fast bacteria using the oligonucleotide combinations in Example 1. Lane 1: the positive standard of the 16S rRNA of *Mycobacterium tuberculosis* ($10^4$ copies). Lane 2: *M. marinum*. Lane 3: *M. kansasii*. Lane 4: *M. intracellulare*. Lane 5: *M. gordonae*. Lane 6: *M. gastri*. Lane 7: *M. terrae*. Lane 8: *M. xenopi*. Lane 9: *M. microti*. Lane 10: *M. nonchromogenicum*. Lne 11: *M. scrofulaceum*. Lane 12: *M. africanum*. Lane 13: *M. szulgai*. Lane 14: *M. avium*. Lane 15: *M. tuberculosis*. Lane N: negative control (containing the diluent instead of a nucleic acid extract). The molecular weight marker was φX174/HaeIII digest (Marker 4, Nippon Gene) (Lane M). The arrows indicate the bands of the amplification products specifically obtained by using the respective combinations of oligonucleotides. In FIG. 2(A) [the combination (a)], the nucleic acid extracts from all the acid-fast bacteria gave specific bands, while in FIG. 2(B) [the combination (b)], tuberculous acid-fast bacteria (*M. tuberculosis, M. africanum* and *M. microti*) and *M. marinum* gave specific bands.

FIG. 3 is a graph correlating the reaction time and the fluorescence enhancement accompanying RNA synthesis from *M. tuberculosis* suspensions in negative sputum at initial concentrations of from 4 to $4 \times 10^6$ cells/1 mL [(A): the combination (a), (B): the combination (b)]. The combination (a) and the combination (b) could detect the sample at $4 \times 10^3$ cells/1 mL (sputum) and 4 cells/1 mL (sputum), respectively.

Now, the present invention will be described in detail.

The present invention may be applied to any of the 5S rRNA, the 16S rRNA and the 23S rRNA, preferably to the 16S rRNA, because 16S rRNA sequences have been reported most in terms of the number of species of acid-fast bacteria.

The regions of the 16S rRNA distinctive of a specific acid-fast bacterium can be identified by investigating the base sequence obtained from a genetic data bank or the like, though, and they are preferably the regions between base 70 and base 200 (in the base sequence of the 16S rRNA from *Mycobacterium tuberculosis* (GenBank No. Z83862)), more preferably the region between base 7 and base 92 which corresponds to SEQ ID NOS:1, 3, 5 and 7 and the region between base 183 and base 200 which corresponds to SEQ ID NOS:2, 4, 6 and 8 (wherein the bases are numbered from the starting position of the 16S rRNA from *Mycobacterium tuberculosis* in the sequence Z83862).

The amplification step in the present invention includes PCR, NASBA, 3SR and TRC (for example, Japanese unexamined patent publication JP-A-2000-14400). Especially, an isothermal nucleic acid amplification method such as NASBA, 3SR or TRC which allows a 16S rRNA sequence by the cooperative action of a reverse transcriptase and an RNA polymerase (under such conditions that the reverse transcriptase and the RNA polymerase act cooperatively). The temperature is preferably from 35 to 50° C., though there is no particular restriction.

In the above-mentioned amplification step, even if the specific sequence is not present at the 5' end of the 16S rRNA, the 16S rRNA can be amplified by adding an oligonucleotide complementary to a region of the 16S rRNA of the specific acid-fast bacterium which flanks the 5' end of the specific sequence with an overlap (of from 1 to 10 bases) with the specific sequence to cleave the 16S rRNA at the 5' end of the specific sequence (by the action of an enzyme having a ribonuclease H activity) before it is used as the template in the initial stage of the nucleic acid amplification. For the cleavage, an oligonucleotide of SEQ ID NO:10 may be used . The scissor oligonucleotide for the cleavage is preferred to have a chemically modified hydroxyl group (for example, an aminated hydroxyl group) at the 3' end so as not to elongate from the 3' end.

Detection of the amplification product obtained in the nucleic acid amplification step is preferably carried out by measuring the change in the fluorescence of the reaction solution during the amplification step in the presence of an oligonucleotide labeled with a fluorescent intercalative dye, though it can be detected by conventional methods for detection of nucleic acid. The oligonucleotide may be, for example, an oligonucleotide having a fluorescent intercalative dye linked to a phosphorus atom in it via a linker. Such an oligonucleotide alters its fluorescence upon formation of a double strand with the target nucleic acid (a complementary nucleic acid) through intercalation of the intercalator moiety into the double strand and is characterized in that it obviates the need for separation analysis (Ishiguro, T. et al., (1996) Nucleic Acids Res. 24 (24) 4992–4997).

The sequence of the oligonucleotide is a sequence distinctive of a specific acid-fast bacterium or common to acid-fast bacteria without particular restrictions. But, it is preferably a sequence consisting of or complementary to at least 10 consecutive bases in SEQ ID NO:9. It is also preferred to chemically modify the hydroxyl group at the 3' end of the oligonucleotide (for example, by adding glycolic acid) to prevent elongation reaction using the oligonucleotide as a primer.

Thus, amplification and detection of an RNA having the same sequence as the specific sequence in the 16S rRNA of the specific acid-fast bacterium can be carried out in one tube at constant temperature in one step and can be automated easily.

Now, the present invention will be described in further detail by referring to Examples. However, the present invention is by no means restricted to these specific Examples.

EXAMPLE 1

Figure 1A:
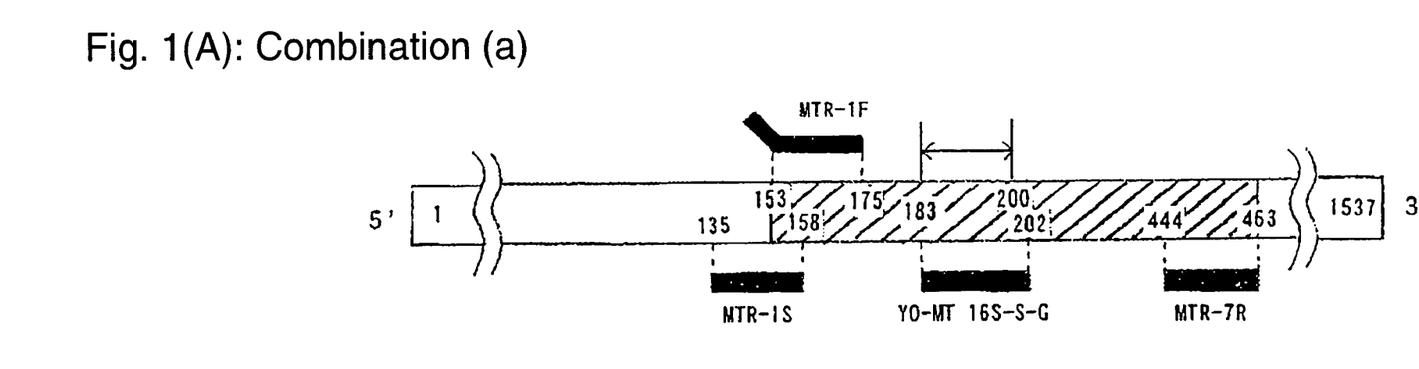
Figure 1B:
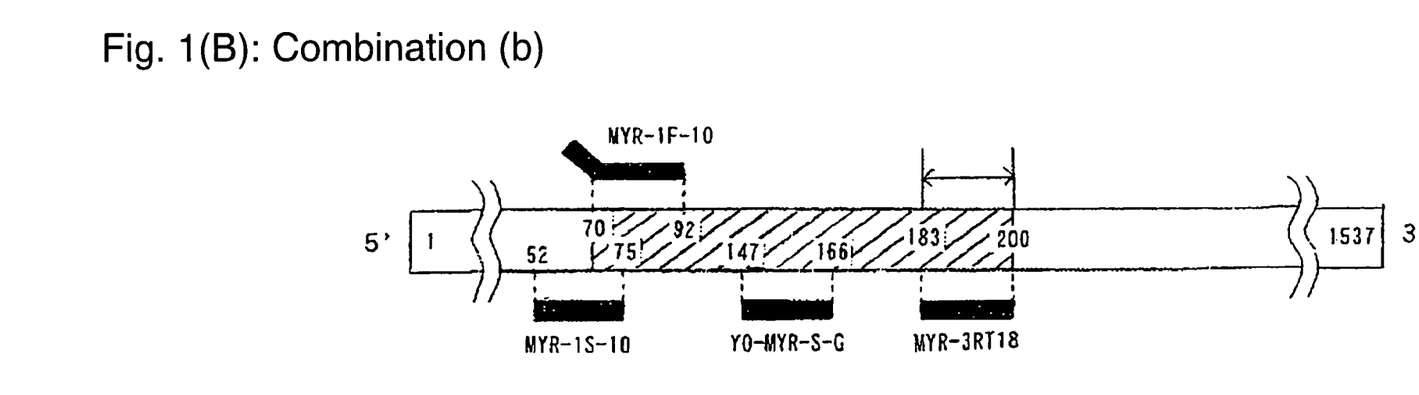
Figure 2A:
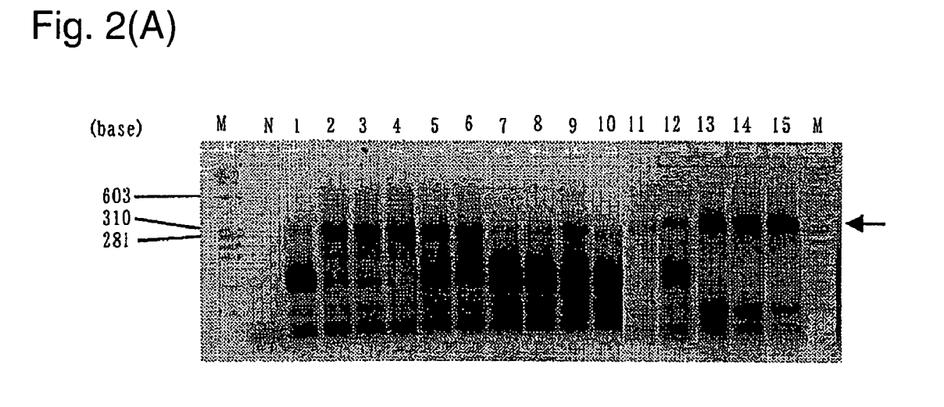
Figure 2B:
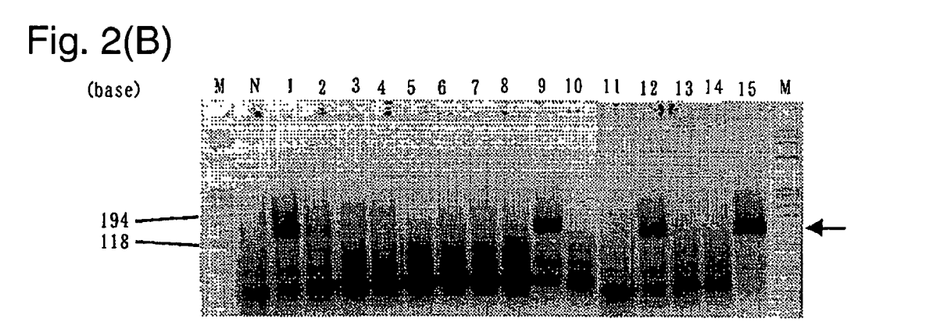

The specificity of the combinations (a) and (b) shown in FIG. 1 for *Mycobacterium tuberculosis* was verified.

(1) Colonies of the following bacteria were suspended in distilled water for injection containing guanidine isocyanate and stirred with glass beads (from 150 to 212 μm, Sigma) for 5 minutes. Then, nucleic acid was extracted from the cell suspensions with Extragen (Tosoh) to obtain acid-fast bacterium nucleic acid extracts.

List of the Test Samples

*M. marinum* (ATCC 927)
*M. kansasii* (ATCC 12478)
*M. intracellulare* (ATCC 13950)
*M. gordonae* (ATCC 14470)
*M. gastri* (ATCC 15754)
*M. terrae* (ATCC 15755)
*M. xenopi* (ATCC 19250)
*M. microti* (ATCC 19422)
*M. nonchromogenicum* (ATCC 19530)
*M. scrofulaceum* (ATCC 19981)
*M. africanum* (ATCC 25420)
*M. szulgai* (ATCC 35799)
*M. avium* (clinical isolate)
*Mycobacterium tuberculosis* (clinical isolate)

(2) 20 μL portions of reaction solutions of the following composition were dispensed into PCR tubes (capacity 0.5 mL: Gene Amp Thin-Walled Reaction Tubes, Perkin Elmer), and 5 μL of the nucleic acid extracts were added thereto. The solutions were prepared so as to contain first, second and third oligonucleotides and an oligonucleotide labeled with an intercalative dye in the combinations shown in Table 1.

The composition of the reaction solutions (in terms of the concentrations in the final volume of 30 μL)

| | |
|---|---|
| 60 mM | Tris-HCl buffer (pH 8.6) |
| 17 mM | Magnesium chloride |
| 100 mM | Potassium chloride |
| 6 U | RNase Inhibitor (Takara Bio) |
| 1 mM | DTT |
| 0.25 mM | each of dATP, dCTP, dGTP and dTTP |
| 3.6 mM | ITP |
| 3.0 mM | each of ATP, CTP, GTP and UTP |
| 0.16 μM | First oligonucleotide |
| 1.0 μM | Second oligonucleotide |
| 1.0 μM | Third oligonucleotide |
| 25 nM | Oligonucleotide labeled with a fluorescent intercalative dye |
| 13% | DMSO |

Distilled water for volume adjustment (3) The reaction solutions were incubated at 44° C. for 5 minutes, and 5 μL of an enzyme solution of the following composition which was pre-incubated at 44° C. for 2 minutes was added.

The composition of the enzyme solution (in terms of the concentrations in the final volume of 30 μL)

| | |
|---|---|
| 2.0% | Sorbitol |
| 3.6 μg | Bovine serum albumin |
| 142 U | T7 RNA polymerase (Invitrogen) |
| 6.4 U | AMV reverse transcriptase (Takara Bio Co., Ltd.) |

Distilled water for volume adjustment (4) Subsequently, the reaction solutions in the PCR tubes were directly monitored at 44° C. in a thermostatic fluorescent spectrophotometer at an excitation wavelength of 470 nm and an emission wavelength of 520 nm.

(5) The rise time for each nucleic acid extract (the time required until the ratio of fluorescence intensity reached 1.2 times the sum of the negative average and triple the standard deviation) is shown in Table 2. The results of electrophoresis (negative photograph) are shown in FIG. 2. The rise times indicated that the combination (a) using an oligonucleotide labeled with a fluorescent intercalative dye for recognition detected specifically tuberculous acid-fast bacteria (*Mycobacterium tuberculosis, M. africanum* and *M. microti*) and the combination (b) using the oligonucleotide of the present invention detected specifically tuberculous acid-fast bacteria (*Mycobacterium tuberculosis, M. africanum* and *M. microti*) and *M. marinum.*

(6) The regions of the RNA amplified in the reaction were identified by agarose gel electrophoresis (agarose concentration 4%) followed by staining with SYBR Green II (Takara Bio). According to the results of the electrophoresis, in the case of the combination (a), specific amplification products were obtained from all the nucleic acid extracts, while in the case of the combination (b), tuberculous acid-fast bacteria (*Mycobacterium tuberculosis, M. africanum* and *M. microti*) gave clear specific amplification bands, and *M. marinum* gave a slight band of the amplification.

TABLE 1

| Combination | First oligo-nucleotide | Second oligo-nucleotide | Third oligo-nucleotide | Intercalative dye-labeled oligo-nucleotide | Length of amplification product (bases) |
|---|---|---|---|---|---|
| (a) | MTR-1S | MTR-1F | MTR-7R | YO-MT 16S-S-G | 317 |
| (b) | MYR-1S-10 | MYR-1F-10 | MYR-3RT18 | YO-MYR-S-G | 137 |

Table 1 shows the combinations of the first, second and third oligonucleotides and the intercalative dye-labeled oligonucleotide used in Examples 1 and 2 and the lengths of the amplification products obtained by using them as specific bands. The regions of the respective combinations of oligonucleotides and the amplified regions are located on the 16S rRNA from *Mycobacterium tuberculosis* as shown in FIG. 1. The base sequences of the first oligonucleotides had aminated hydroxyl groups at the 3' end. The second oligonucleotides had base sequences which additionally had the T7 promoter region at the 5' end from "A" at position 1 from the 5' end to "A" at position 22 and the subsequent enhancer sequence from "G" at position 23 to "A" at position 28. Among the intercalative dye-labeled oligonucleotides, YO-MT 16S-S-G (SEQ ID NO:15) had an intercalative dye as the label between "C" at position 16 from the 5' end and "C" at position 17, and YO-MYR-S-G (SEQ ID NO:9) had an intercalative dye as the label between "A" at position 7 from the 5' end and "G" at position 8, and they had hydroxyl groups modified with glycolic acid at the 3' end.

The First Oligonucleotides
  MTR-1S (SEQ ID NO:11, from base 135 to base 158)
  MYR-1S-10 (SEQ ID NO:10, from base 52 to base 75)

The Second Oligonucleotides
  MTR-1F (SEQ ID NO:12, from base 153 to base 175)
  MYR-1F-10 (SEQ ID NO:13, from base 70 to base 92)

The Third Oligonucleotides
  MTR-7R (SEQ ID NO:14, from 444 to base 463)
  MYR-3RT18 (SEQ ID NO:2, from base 183 to base 200)

The Intercalative Dye-labeled Oligonucleotides
  YO-MT 16S-S-G (SEQ ID NO:15, from base 183 to base 202)
  YO-MYR-S-G (SEQ ID NO:9, from base 147 to base 166)

TABLE 2

| Acid-fast bacterium | Rise time (min) | |
| --- | --- | --- |
| sample | Combination (a) | Combination (b) |
| M. marinum | N.D. | 11.6 |
| M. kansasii | N.D. | N.D. |
| M. intracellulare | N.D. | N.D. |
| M. gordonae | N.D. | N.D. |
| M. gastri | N.D. | N.D. |
| M. terrae | N.D. | N.D. |
| M. xenopi | N.D. | N.D. |
| M. microti | 28.2 | 8.5 |
| M. nonchromogenicum | N.D. | N.D. |
| M. scrofulaceum | N.D. | N.D. |
| M. africanum | 30.6 | 9.1 |
| M. szulgai | N.D. | N.D. |
| M. avium | N.D. | N.D. |
| M. tuberculosis | 17.3 | 6.2 |

Table 2 shows the results of the analyses of the nucleotide extracts from acid-fast bacteria using the respective oligonucleotide combinations. The results are represented in terms of rise time. N.D. in the table indicates that the sample gave no rise (was not detected) within 60 minutes with the combination (a) or within 20 minutes with the combination (b). With the combination (a), tuberculous acid-fast bacteria (*Mycobacterium tuberculosis*, *M. africanum* and *M. microti*) were detected, and with the combination (b), tuberculous acid-fast bacteria (*Mycobacterium tuberculosis*, *M. africanum* and *M. microti*) and *M. marinum* were detected.

EXAMPLE 2

*Mycobacterium tuberculosis* at various cell concentrations in sputum were detected with the combination (a) using an oligonucleotide labeled with a fluorescent intercalative dye for recognizing the specificity and the combination (b) of the present invention.

(1) *Mycobacterium tuberculosis* suspensions containing from 4 to 4×10$^6$ cells in 1 mL of control sputum were used as samples for measurement of the sensitivity limit for *Mycobacterium tuberculosis* in sputum. The samples were treated with NALC, and then with guanidine isocyanate and glass beads (from 150 to 212 μm, Sigma), and nucleic acid was extracted from the resulting solutions with Extragen (Tosoh).

(2) 20 μL portions of a reaction solution of the following composition were dispensed into PCR tubes (capacity 0.5 mL: Gene Amp Thin-Walled Reaction Tubes, Perkin Elmer), and 5 μL of the nucleic acid extracts were added thereto. The solutions were prepared so as to contain first, second and third oligonucleotides and the oligonucleotide labeled with an intercalative dye in the combinations shown in Table 1.

The composition of the reaction solution (in terms of the concentrations in the final volume of 30 μL)

| | |
| --- | --- |
| 60 mM | Tris-HCl buffer (pH 8.6) |
| 17 mM | Magnesium chloride |
| 120 mM | Potassium chloride |
| 6 U | RNase Inhibitor (Takara Bio) |
| 1 mM | DTT |
| 0.25 mM | each of dATP, dCTP, dGTP and dTTP |
| 3.6 mM | ITP |
| 3.0 mM | each of ATP, CTP, GTP and UTP |
| 0.16 μM | First oligonucleotide |
| 1.0 μM | Third oligonucleotide |
| 25 nM | Oligonucleotide labeled with a fluorescent intercalative dye |
| 13% | DMSO |

Distilled water for volume adjustment (3) The reaction solutions were incubated at 44° C. for 5 minutes, and 5 μL of an enzyme solution of the following composition which was pre-incubated at 44° C. for 2 minutes was added.

The composition of the enzyme solution (in terms of the concentrations in the final volume of 30 μL)

| | |
| --- | --- |
| 2.0% | Sorbitol |
| 3.6 μg | Bovine serum albumin |
| 142 U | T7 RNA polymerase (Invitrogen) |
| 6.4 U | AMV reverse transcriptase (Takara Bio) |

Distilled water for volume adjustment (4) Subsequently, the reaction solutions in the PCR tubes were directly monitored at 44° C. in a thermostatic fluorescent spectrophotometer at an excitation wavelength of 470 nm and an emission wavelength of 520 nm.

Figure 3A:
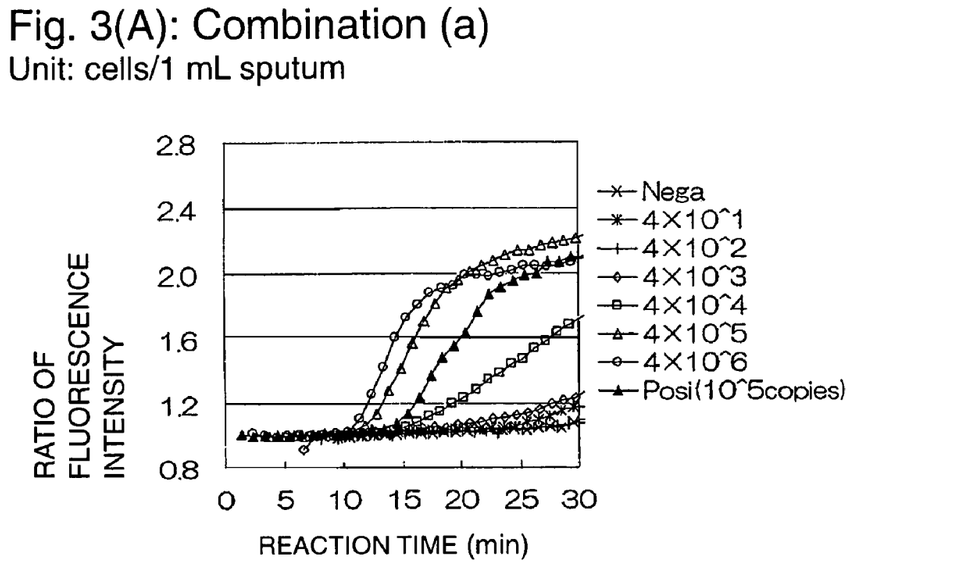
Figure 3B:
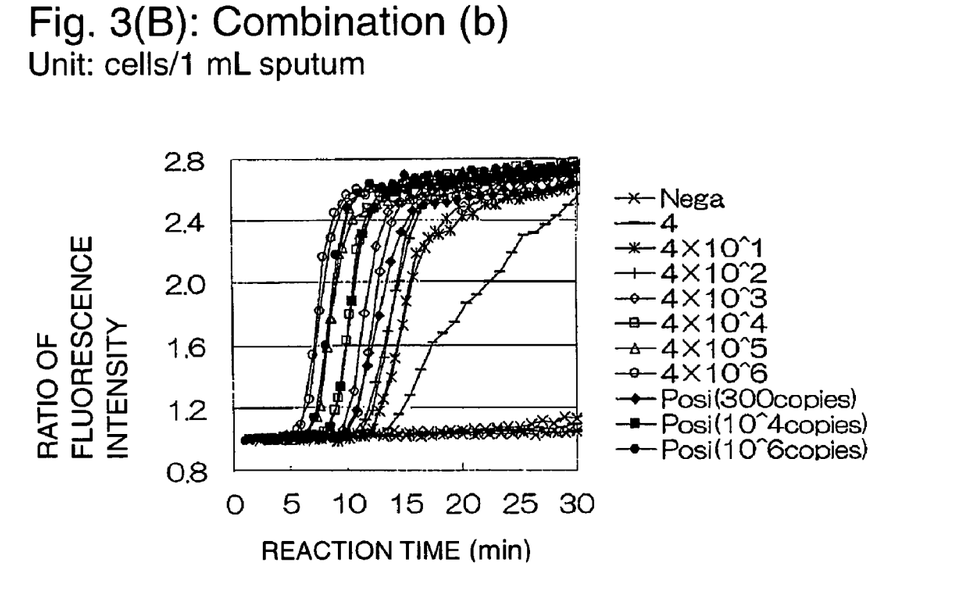

(5) The time courses of the ratio of fluorescence intensities of the samples (fluorescence intensity at a certain time/background fluorescence intensity) from addition of the enzyme solution at 0 minute were shown in FIG. 3, and the results obtained with the respective samples were shown in Table 3. The results suggest that the sensitivity limit of the detection using the oligonucleotide combination of the present invention [the combination (b)] was 4 cells/1 mL (sputum) and higher than that using the combination (a) using an intercalative dye-labeled oligonucleotide for recognition of specificity [4×10³ cells/1 mL (sputum)]. The results obtained with the oligonucleotide combination of the present invention [the combination (b)] and the sensitivity limit of a commercially available kit (Product name: Amplicore *Mycobacterium tuberclosis*, Roche Diagnostics) are compared in Table 3. It is confirmed that the sensitivity limit of the reagent using the oligonucleotide combination of the present invention is high as compared with the commercially available kit.

TABLE 3

| Number of *M. tuberculosis* cells (cells/1 mL of sputum) | Detectability | | |
|---|---|---|---|
| | Combination (a) | Combination (b) | Commercially available kit |
| 4 × 10⁶ | Detected | Detected | Detected |
| 4 × 10⁵ | Detected | Detected | Detected |
| 4 × 10⁴ | Detected | Detected | Detected |
| 4 × 10³ | Detected | Detected | Detected |
| 4 × 10² | N.D. | Detected | Detected |
| 4 × 10¹ | N.D. | Detected | N.D. |
| 4 | N.D. | Detected | N.D. |
| 0 | N.D. | N.D. | N.D. |

Table 3 shows the results of the measurements of the *Mycobacterium tuberculosis* cells in sputum using the respective oligonucleotide combinations [the combinations (a) and (b)] and a commercially available kit (product name: Amplicore *Mycobacterium tuberculosis*). The combinations (a) and (b) are considered to have succeeded in detection when they gave a rise within 30 minutes. The sensitivity limit was 4×10³ cells/1 mL (sputum) for the combination (a), 4 cells/1 mL (sputum) for the combination (b) and 4×10² cells/1 mL (sputum) for the commercially available kit.

EXAMPLE 3

The specificity of the oligonucleotide combination of the present invention for the nontuberculous acid-fast bacterium *Mycobacterium avium* was confirmed.

(1) Colonies of various bacteria shown below were suspended in distilled water for injection containing guanidine isocyanate and stirred with glass beads (from 150 to 212 µm, Sigma) for 5 minutes. Then, nucleic acid was extracted from the cell suspensions with Extragen (Tosoh) to obtain acid-fast bacteria nucleic acid extracts.

List of the Test Samples
  *M. marinum* (ATCC 927)
  *M. fortuitum* (ATCC 6841)
  *M. kansasii* (ATCC 12478)
  *M. intracellulare* (ATCC 13950)
  *M. peregrinum* (ATCC 14467)
  *M. gordonae* (ATCC 14470)
  *M. gastri* (ATCC 15754)
  *M. terrae* (ATCC 15755)
  *M. xenopi* (ATCC 19250)
  *M. microti* (ATCC 19422)
  *M. nonchromogenicum* (ATCC 19530)
  *M. abscessus* (ATCC 19977)
  *M. scrofulaceum* (ATCC 19981)
  *M. triviale* (ATCC 23292)
  *M. simiae* (ATCC 25275)
  *M. africanum* (ATCC 25420)
  *M. chelonae* (ATCC 35752)
  *M. szulgai* (ATCC 35799)
  *M. avium* (clinical isolate)
  *Mycobacterium tuberculosis* (clinical isolate)

(2) 20 µL portions of a reaction solution of the following composition were dispensed into PCR tubes (capacity 0.5 mL: Gene Amp Thin-Walled Reaction Tubes, Perkin Elmer), and 5 µL of the nucleic acid extracts were added thereto.

The composition of the reaction solution (in terms of the concentrations in the final volume of 30 µL)

| | |
|---|---|
| 60 mM | Tris-HCl buffer (pH 8.6) |
| 17 mM | Magnesium chloride |
| 100 mM | Potassium chloride |
| 6 U | RNase Inhibitor (Takara Bio Co., Ltd.) |
| 1 mM | DTT |
| 0.25 mM | each of dATP, dCTP, dGTP and dTTP |
| 3.6 mM | ITP |
| 3.0 mM | each of ATP, CTP, GTP and UTP |
| 0.16 µM | First oligonucleotide (MYR-1S-10, SEQ ID NO: 10, having an aminated hydroxyl group at the 3' end) |
| 1.0 µM | Second oligonucleotide (MYR-1FA-10, SEQ ID NO: 16, wherein the region from "A" at position 1 from the 5' end to "A" at position 22 is the T7 promoter region, and the subsequent region from "G" at position 23 to "A" at position 28 is the enhancer sequence) |
| 1.0 µM | Third oligonucleotide (MYR-3RA18, SEQ ID NO: 4) |
| 25 nM | Oligonucleotide labeled with a fluorescent intercalative dye (YO-MYR-S-G, SEQ ID NO: 9, having an intercalative dye as the label between "A" at position 7 from the 5' end and "G" at position 8 and a hydroxyl group modified with glycolic acid at the 3' end) |
| 13% | DMSO |

Distilled water for volume adjustment (3) The reaction solutions were incubated at 44° C. for 5 minutes, and 5 µL of an enzyme solution of the following composition which was pre-incubated at 44° C. for 2 minutes was added.

The composition of the enzyme solution (in terms of the concentrations in the final volume of 30 µL)

| | |
|---|---|
| 2.0% | Sorbitol |
| 3.6 µg | Bovine serum albumin |
| 142 U | T7 RNA polymerase (Invitrogen) |
| 6.4 U | AMV reverse transcriptase (Takara Bio Co., Ltd.) |

Distilled water for volume adjustment (4) Subsequently, the reaction solutions in the PCR tubes were directly monitored at 44° C. in a thermostatic fluorescent spectrophotometer at an excitation wavelength of 470 nm and an emission wavelength of 520 nm.

(5) The rise time for each nucleic acid extract (the time required until the ratio of fluorescence intensity reached 1.2 times the sum of the negative average and triple the standard deviation) is shown in Table 4. These results indicate that the oligonucleotide combination of the present invention specifically detects *M. avium*.

TABLE 4

| Acid-fast bacterium sample | Rise time (min) |
|---|---|
| *M. marinum* | N.D. |
| *M. fortuitum* | N.D. |
| *M. kansasii* | N.D. |
| *M. intracellulare* | N.D. |
| *M. peregrinum* | N.D. |
| *M. gordonae* | N.D. |
| *M. gastri* | N.D. |
| *M. terrae* | N.D. |
| *M. xenopi* | N.D. |
| *M. microti* | N.D. |
| *M. nonchromogenicum* | N.D. |
| *M. abscessus* | N.D. |
| *M. scrofulaceum* | N.D. |
| *M. triviale* | N.D. |
| *M. simiae* | N.D. |
| *M. africanum* | N.D. |
| *M. chelonae* | N.D. |
| *M. szulgai* | N.D. |
| *M. avium* | 9.1 |
| *M. tuberculosis* | N.D. |

Table 4 shows the results of the measurements of the nucleic acid extracts from acid-fast bacteria using the oligonucleotide combination of the present invention. The results are represented in terms of rise time. N.D. in the table indicates that the sample gave no rise (was not detected) within 20 minutes. With the oligonucleotide combination of the present invention, *M. avium* was detected specifically.

EXAMPLE 4

The specificity of the oligonucleotide combination of the present invention for the nontuberculous acid-fast bacterium *Mycobacterium intracellulare* was confirmed.

(1) Colonies of various bacteria shown below were suspended in distilled water for injection containing guanidine isocyanate and stirred with glass beads (from 150 to 212 μm, Sigma) for 5 minutes. Then, nucleic acid was extracted from the cell suspensions with Extragen (Tosoh) to obtain acid-fast bacteria nucleic acid extracts.

List of the Test Samples

*M. marinum* (ATCC 927)
*M. fortuitum* (ATCC 6841)
*M. kansasii* (ATCC 12478)
*M. intracellulare* (ATCC 13950)
*M. peregrinum* (ATCC 14467)
*M. gordonae* (ATCC 14470)
*M. gastri* (ATCC 15754)
*M. terrae* (ATCC 15755)
*M. xenopi* (ATCC 19250)
*M. microti* (ATCC 19422)
*M. nonchromogenicum* (ATCC 19530)
*M. abscessus* (ATCC 19977)
*M. scrofulaceum* (ATCC 19981)
*M. triviale* (ATCC 23292)
*M. simiae* (ATCC 25275)
*M. africanum* (ATCC 25420)
*M. chelonae* (ATCC 35752)
*M. szulgai* (ATCC 35799)
*M. avium* (clinical isolate)
*Mycobacterium tuberculosis* (clinical isolate)

(2) 20 μL portions of a reaction solution of the following composition were dispensed into PCR tubes (capacity 0.5 mL: Gene Amp Thin-Walled Reaction Tubes, Perkin Elmer), and 5 μL of the nucleic acid extracts were added thereto.

The composition of the reaction solution (in terms of the concentrations in the final volume of 30 μL)

| 60 mM | Tris-HCl buffer (pH 8.6) |
|---|---|
| 17 mM | Magnesium chloride |
| 100 mM | Potassium chloride |
| 6 U | RNase Inhibitor (Takara Bio) |
| 1 mM | DTT |
| 0.25 mM | each of dATP, dCTP, dGTP and dTTP |
| 3.6 mM | ITP |
| 3.0 mM | each of ATP, CTP, GTP and UTP |
| 0.16 μM | First oligonucleotide (MYR-1S-10, SEQ ID NO: 10, having an aminated hydroxyl group at the 3' end) |
| 1.0 μM | Second oligonucleotide (MYR-1FI-10, SEQ ID NO: 17, wherein the region from "A" at position 1 from the 5' end to "A" at position 22 is the T7 promoter region, and the subsequent region from "G" at position 23 to "A" at position 28 is the enhancer sequence) |
| 1.0 μM | Third oligonucleotide (MYR-3RI18, SEQ ID NO: 6) |
| 25 nM | Oligonucleotide labeled with a fluorescent intercalative dye (YO-MYR-S-G, SEQ ID NO: 9, having an intercalative dye as the label between "A" at position 7 from the 5' end and "G" at position 8 and a hydroxyl group modified with glycolic acid at the 3' end) |
| 13% | DMSO |

Distilled water for volume adjustment (3) The reaction solutions were incubated at 44° C. for 5 minutes, and 5 μL of an enzyme solution of the following composition which was pre-incubated at 44° C. for 2 minutes was added.

The composition of the enzyme solution (in terms of the concentrations in the final volume of 30 μL)

| 2.0% | Sorbitol |
|---|---|
| 3.6 μg | Bovine serum albumin |
| 142 U | T7 RNA polymerase (Gibco) |
| 6.4 U | AMV reverse transcriptase (Takara Bio Co., Ltd.) |

Distilled water for volume adjustment (4) Subsequently, the reaction solutions in the PCR tubes were directly monitored at 44° C. in a thermostatic fluorescent spectrophotometer at an excitation wavelength of 470 nm and an emission wavelength of 520 nm.

(5) The rise time for each nucleic acid extract (the time required until the ratio of fluorescence intensity reached 1.2 times the sum of the negative average and triple the standard deviation) is shown in Table 5. These results indicate that the oligonucleotide combination of the present invention specifically detects *M. intracellulare*.

TABLE 5

| Acid-fast bacterium sample | Rise time (min) |
| --- | --- |
| M. marinum | N.D. |
| M. fortuitum | N.D. |
| M. kansasii | N.D. |
| M. intracellulare | 12.4 |
| M. peregrinum | N.D. |
| M. gordonae | N.D. |
| M. gastri | N.D. |
| M. terrae | N.D. |
| M. xenopi | N.D. |
| M. microti | N.D. |
| M. nonchromogenicum | N.D. |
| M. abscessus | N.D. |
| M. scrofulaceum | N.D. |
| M. triviale | N.D. |
| M. simiae | N.D. |
| M. africanum | N.D. |
| M. chelonae | N.D. |
| M. szulgai | N.D. |
| M. avium | N.D. |
| M. tuberculosis | N.D. |

Table 5 shows the results of the measurements of the nucleic acid extracts from acid-fast bacteria using the oligonucleotide combination of the present invention. The results are represented in terms of rise time. N.D. in the table that the sample gave no rise (was not detected) within 20 minutes. With the oligonucleotide combination of the present invention, M. intracellulare was detected specifically.

EXAMPLE 5

The specificity of the oligonucleotide combination of the present invention for the nontuberculous acid-fast bacterium Mycobacterium kansasii was confirmed.

(1) Colonies of various bacteria shown below were suspended in distilled water for injection containing guanidine isocyanate and stirred with glass beads (from 150 to 212 μm, Sigma) for 5 minutes. Then, nucleic acid was extracted from the cell suspensions with Extragen (Tosoh) to obtain acid-fast bacteria nucleic acid extracts.

List of the Test Samples
  M. marinum (ATCC 927)
  M. fortuitum (ATCC 6841)
  M. kansasii (ATCC 12478)
  M. intracellulare (ATCC 13950)
  M. peregrinum (ATCC 14467)
  M. gordonae (ATCC 14470)
  M. gastri (ATCC 15754)
  M. terrae (ATCC 15755)
  M. xenopi (ATCC 19250)
  M. microti (ATCC 19422)
  M. nonchromogenicum (ATCC 19530)
  M. abscessus (ATCC 19977)
  M. scrofulaceum (ATCC 19981)
  M. triviale (ATCC 23292)
  M. simiae (ATCC 25275)
  M. africanum (ATCC 25420)
  M. chelonae (ATCC 35752)
  M. szulgai (ATCC 35799)
  M. avium (clinical isolate)
  Mycobacterium tuberculosis (clinical isolate)

(2) 20 μL portions of a reaction solution of the following composition were dispensed into PCR tubes (capacity 0.5 mL: Gene Amp Thin-Walled Reaction Tubes, Perkin Elmer), and 5 μL of the nucleic acid extracts were added thereto.

The composition of the reaction solution (in terms of the concentrations in the final volume of 30 μL)

| 60 mM | Tris-HCl buffer (pH 8.6) |
| 17 mM | Magnesium chloride |
| 100 mM | Potassium chloride |
| 6 U | RNase Inhibitor (Takara Bio) |
| 1 mM | DTT |
| 0.25 mM | each of dATP, dCTP, dGTP and dTTP |
| 3.6 mM | ITP |
| 3.0 mM | each of ATP, CTP, GTP and UTP |
| 0.16 μM | First oligonucleotide (MYR-1S-10, SEQ ID NO: 10, having an aminated hydroxyl group at the 3' end) |
| 1.0 μM | Second oligonucleotide (MYR-1FK-10, SEQ ID NO: 18, wherein the region from "A" at position 1 from the 5' end to "A" at position 22 is the T7 promoter region, and the subsequent region from "G" at position 23 to "A" at position 28 is the enhancer sequence) |
| 1.0 μM | Third oligonucleotide (MYR-3RK18, SEQ ID NO: 8) |
| 25 nM | Oligonucleotide labeled with a fluorescent intercalative dye (YO-MYR-S-G, SEQ ID NO: 9, having an intercalative dye as the label between "A" at position 7 from the 5' end and "G" at position 8 and a hydroxyl group modified with glycolic acid at the 3' end) |
| 13% | DMSO |

Distilled water for volume adjustment (3) The reaction solutions were incubated at 44° C. for 5 minutes, and 5 μL of an enzyme solution of the following composition which was pre-incubated at 44° C. for 2 minutes was added.

The composition of the enzyme solution (in terms of the concentrations in the final volume of 30 μL)

| 2.0% | Sorbitol |
| 3.6 μg | Bovine serum albumin |
| 142 U | T7 RNA polymerase (Gibco) |
| 6.4 U | AMV reverse transcriptase (Takara Bio) |

Distilled water for volume adjustment (4) Subsequently, the reaction solutions in the PCR tubes were directly monitored at 44° C. in a thermostatic fluorescent spectrophotometer at an excitation wavelength of 470 nm and an emission wavelength of 520 nm.

(5) The rise time for each nucleic acid extract (the time required until the ratio of fluorescence intensity reached 1.2 times the sum of the negative average and triple the standard deviation) is shown in Table 6. These results indicate that the oligonucleotide combination of the present invention specifically detects M. kansasii and M. gastri (which has the same 16S rRNA as M. kansasii).

TABLE 6

| Acid-fast bacterium sample | Rise time (min) |
| --- | --- |
| M. marinum | N.D. |
| M. fortuitum | N.D. |
| M. kansasii | 13.4 |
| M. intracellulare | N.D. |
| M. peregrinum | N.D. |
| M. gordonae | N.D. |
| M. gastri | 11.9. |
| M. terrae | N.D. |
| M. xenopi | N.D. |

TABLE 6-continued

| Acid-fast bacterium sample | Rise time (min) |
|---|---|
| M. microti | N.D. |
| M. nonchromogenicum | N.D. |
| M. abscessus | N.D. |
| M. scrofulaceum | N.D. |
| M. triviale | N.D. |
| M. simiae | N.D. |
| M. africanum | N.D. |
| M. chelonae | N.D. |
| M. szulgai | N.D. |
| M. avium | N.D. |
| M. tuberculosis | N.D. |

Table 6 shows the results of the measurements of the nucleic acid extracts from acid-fast bacteria using the oligonucleotide combination of the present invention. The represented in terms of rise time. N.D. in the table that the sample gave no rise (was not detected) within 20 minutes.

With the oligonucleotide combination of the present invention, M. kansasii and M. gastri were detected specifically.

As described above, the detection method of the present invention is useful for specific and high-sensitive detection of the 16S rRNAs from specific acid-fast bacteria.

The oligonucleotides of the present invention are not restricted to the base sequences (consisting of 18 bases to 23 bases) shown in the Sequence Listing and may be oligonucleotides consisting of at least 10 consecutive bases in these sequences and have extremely high specificity for the target nucleic acid. These oligonucleotides or oligonucleotides consisting of at least 10 consecutive bases in them have enough specificity for the target nucleic acid as primers or probes at relatively low temperatures (preferably 44° C.) and the use of the oligonucleotides of the present invention obviously enables isothermal amplification and detection of the rRNA (at relatively low temperatures).

The entire disclosure of Japanese Patent Application No. 2002-368230 filed on Dec. 19, 2002 including specification, claims, drawings and summary is incorporated herein by reference in its entirety.

The invention claimed is:

1. A method of detecting an acid-fast bacterium selected from the group consisting of *Mycobacterium tuberculosis, Mycobacterium avium, Mycobacterium intracellulare* and *Mycobacterium kansasii*, comprising:
  (a) performing a nucleotide amplification reaction on a mixture comprising
    (i) a test sample comprising rRNA, and
    (ii) a pair of primers consisting of a first primer and a second primer, wherein said primers specifically amplify a region of rRNA sequence that is specific to an acid-fast bacterium selected from the group consisting of *Mycobacterium tuberculosis, Mycobacterium avium, Mycobacterium intracellulare* and *Mycobacterium kansasii*, and
  (b) detecting any resulting specifically amplified rRNA;
  wherein said pair of primers is selected from the group consisting of:
  primer pair (i), wherein said first primer consists essentially of at least 10 consecutive nucleotides of SEQ ID NO:1, or a complement thereof, and said second primer consists essentially of at least 10 consecutive nucleotides of SEQ ID NO:2, or a complement thereof;
  primer pair (ii), wherein said first primer consists essentially of at least 10 consecutive nucleotides of SEQ ID NO:3, or a complement thereof, and said second primer consists essentially of at least 10 consecutive nucleotides of SEQ ID NO:4, or a complement thereof;
  primer pair (iii), wherein said first primer consists essentially of at least 10 consecutive nucleotides of SEQ ID NO:5, or a complement thereof, and said second primer consists essentially of at least 10 consecutive nucleotides of SEQ ID NO:6, or a complement thereof; and
  primer pair (iv), wherein said first primer consists essentially of at least 10 consecutive nucleotides of SEQ ID NO:7, or a complement thereof, and said second primer consists essentially of at least 10 consecutive nucleotides of SEQ ID NO:8, or a complement thereof.

2. A method of amplifying 16S rRNA from an acid-fast bacterium selected from the group consisting of *Mycobacterium tuberculosis, Mycobacterium avium, Mycobacterium intracellulare* and *Mycobacterium kansasii*, comprising:
  (a) using 16S rRNA from an acid-fast bacterium selected from the group consisting of *Mycobacterium tuberculosis, Mycobacterium avium, Mycobacterium intracellulare* and *Mycobacterium kansasii* as a template, synthesizing a first complementary DNA strand with an RNA-dependent DNA polymerase to thereby obtain an RNA-DNA double-stranded molecule,
  (b) degrading the 16S rRNA in said RNA-DNA double stranded molecule of (a) using an enzyme having ribonuclease H activity to thereby obtain a single-stranded DNA molecule,
  (c) using said single-stranded DNA molecule of (b) as a template, synthesizing a second complementary DNA strand using a DNA-dependent DNA polymerase to thereby obtain a double-stranded DNA molecule having a promoter sequence for a DNA-dependent RNA polymerase,
  (d) using said double-stranded DNA molecule of (c) as a template, transcribing a complementary RNA strand using a DNA-dependent RNA polymerase to thereby obtain an RNA transcript, and
  (e) repeating (a)–(d) using said RNA transcript as a template,
  wherein said method is carried out using at least one primer comprising a promoter sequence for DNA-dependent RNA polymerase at the 5' end of said primer, and
  wherein said method is carried out using a pair of primers consisting of a first primer and a second primer,
  wherein said pair of primers is selected from the group consisting of:
  primer pair (i), wherein said first primer consists essentially of at least 10 consecutive nucleotides of SEQ ID NO:1, or a complement thereof, and said second primer consists essentially of at least 10 consecutive nucleotides of SEQ ID NO:2, or a complement thereof;
  primer pair (ii), wherein said first primer consists essentially of at least 10 consecutive nucleotides of SEQ ID NO:3, or a complement thereof, and said second primer consists essentially of at least 10 consecutive nucleotides of SEQ ID NO:4, or a complement thereof;
  primer pair (iii), wherein said first primer consists essentially of at least 10 consecutive nucleotides of SEQ ID NO:5, or a complement thereof, and said second primer consists essentially of at least 10 consecutive nucleotides of SEQ ID NO:6, or a complement thereof; and
  primer pair (iv), wherein said first primer consists essentially of at least 10 consecutive nucleotides of SEQ ID NO:7, or a complement thereof, and said second primer consists essentially of at least 10 consecutive nucleotides of SEQ ID NO:8, or a complement thereof.

3. The method according to claim 1 or 2, wherein said specific acid-fast bacteria is *Mycobacterium tuberculosis*, and wherein said primer pair is primer pair (i).

4. The method according to claim 1 or 2, wherein said specific acid-fast bacterium is *Mycobacterium avium*, and wherein said primer pair is primer pair (ii).

5. The method according to claim 1 or 2, wherein the specific acid-fast bacterium is *Mycobacterium intracellulare*, and wherein said primer pair is primer pair (iii).

6. The method according to claim 1 or 2, wherein said specific acid-fast bacterium is *Mycobacterium kansasii*, and wherein said primer pair is primer pair (iv).

7. The method according to claim 2, which further comprises the step of:

(f) detecting said RNA transcript using an oligonucleotide probe which specifically binds to said RNA transcript, wherein said oligonucleotide probe is labeled with a fluorescent intercalative dye, wherein said oligonucleotide probe has a sequence different from that of said first primer and said second primer, and wherein said detecting is carried out by measuring a change in fluorescence of said oligonucleotide probe.

8. The method according to claim 7, wherein said oligonucleotide probe is labeled with a fluorescent intercalative dye whose fluorescence is altered upon hybridization.

9. The method according to claim 8, wherein said oligonucleotide probe consists essentially of at least 10 consecutive nucleotides of SEQ ID NO:9, or a complement thereof.

10. The method according to claims 1 or 2, wherein said primer pair (i) consists of SEQ ID NO:13 and SEQ ID NO:2.

11. The method according to claims 1 or 2, wherein said primer pair (ii) consists of SEQ ID NO:16 and SEQ ID NO:4.

12. The method according to claims 1 or 2, wherein said primer pair (iii) consists of SEQ ID NO:17 and SEQ ID NO:6.

13. The method according to claims 1 or 2, wherein said primer pair (iv) consists of SEQ ID NO:18 and SEQ ID NO:8.

* * * * *